(12) United States Patent
Churovich

(10) Patent No.: US 9,220,635 B2
(45) Date of Patent: Dec. 29, 2015

(54) TACTILE PATTERN MUSIC GENERATOR AND PLAYER

(71) Applicant: Douglas D. Churovich, Des Peres, MO (US)

(72) Inventor: Douglas D. Churovich, Des Peres, MO (US)

( * ) Notice: Subject to any disclaimer, the term of this patent is extended or adjusted under 35 U.S.C. 154(b) by 447 days.

(21) Appl. No.: 13/725,386

(22) Filed: Dec. 21, 2012

(65) Prior Publication Data

US 2013/0162416 A1 Jun. 27, 2013

Related U.S. Application Data

(60) Provisional application No. 61/579,416, filed on Dec. 22, 2011.

(51) Int. Cl.
*H04B 3/36* (2006.01)
*A61F 11/04* (2006.01)
*G09B 21/00* (2006.01)

(52) U.S. Cl.
CPC ............ *A61F 11/045* (2013.01); *G09B 21/003* (2013.01)

(58) Field of Classification Search
CPC ............................. A61F 11/045; G09B 21/003
USPC ........................................................ 340/407.1
See application file for complete search history.

(56) References Cited

U.S. PATENT DOCUMENTS

| | | | |
|---|---|---|---|
| 5,035,242 A * | 7/1991 | Franklin et al. | 607/108 |
| 5,719,561 A * | 2/1998 | Gonzales | 340/7.51 |
| 6,359,550 B1 * | 3/2002 | Brisebois et al. | 340/407.1 |
| 2007/0242040 A1 * | 10/2007 | Ullrich et al. | 345/157 |
| 2008/0284277 A1 | 11/2008 | Kwon et al. | |
| 2009/0293663 A1 | 12/2009 | Chang et al. | |
| 2010/0109486 A1 | 5/2010 | Polyakov et al. | |
| 2010/0197184 A1 | 8/2010 | Browne et al. | |
| 2010/0205803 A1 | 8/2010 | Lipton et al. | |
| 2011/0128132 A1 * | 6/2011 | Ullrich et al. | 340/407.1 |
| 2011/0209599 A1 * | 9/2011 | Aponte | 84/723 |

OTHER PUBLICATIONS

"Applications of See by Touch" article, 2 pages.
Vasily Tarasov, "Kinect for the Blind" web article, ZoneOS, 2011, 5 pages.
Tactile Audio Displays Inc., "True Sound Immersion" web article, 1 page.
Tactile Audio Displays Inc., "Software, Hardware, Form Factors" web article, 1 page.
Tactile Audio Displays Inc., "R&D A Brief History in Time" web article, 1 page.
Daniel A. Begun, ""Feel" the Movies with Philips' Tactile Jacket" web article, IEEE Spectrum news archive, Mar. 20, 2009, 1 page.

(Continued)

*Primary Examiner* — Daryl Pope
(74) *Attorney, Agent, or Firm* — Polster, Lieder, Woodruff & Lucchesi, LC

(57) ABSTRACT

A device that produces patterned tactile sensations or events discernible to human touch from micro-actuators housed in a fabric, or other pliable material, where such actuated sensations or events are discernible by a user donning the fabric. The device is configured to convert electronically stored music or audio data into a sequence of patterned tactile sensations or events in a matrix across the fabric, providing a tactile representation of the music or audio data to the user. The discernible tactile sensations or events may alternately comprise retractable physical features, electric stimuli, and/or combinations of these.

21 Claims, 3 Drawing Sheets

(56) References Cited

OTHER PUBLICATIONS

Wikipedia, "Haptic technology" web article, Wikipedia Foundation, Inc., Dec. 1, 2011, 7 pages.
Michael Kanellos, "Electric Fabric—An Energy Technology Bob Mackie Would Love" web article, Greentech Media, Inc., Sep. 1, 2008, 3 pages.
Paul Eng, "Electric Fabric for Really Soft-Touch Controls" web article, abc News, Jun. 14, 2005, 6 pages.
Danfoss Polypower A/S, "DEAP technology to innovate the solutions that we know today" web article, Danfoss PolyPower A/S, 1 page.
Danfoss Polypower A/S, "Ongoing research activities" web article, Danfoss PolyPower A/S, 1 page.
Danfoss Polypower A/S, "DEAP technology is a platform technology as fundamental as electromagnetic solenoid, piezo ceramics etc." web article, Danfoss PolyPower A/S, 1 page.
Wikipedia, "Electroactive polymers" web article, Wikipedia Foundation, Inc., Oct. 16, 2011, 8 pages.
A. Puertas, P. Pures, A.M. Echenique, J.P. Graffigna, G. Ensinck, "Braille line using electrical stimulation", IOP Publishing Ltd., 2007, Journal of Physics: Conference Series 90 (2007) 012091, 8 pages.
Michael Kozlowski, "E-Readers and technology to assist the Blind", Good E-Reader, Apr. 6, 2 pages.
Darren Murph, "Braille e-reader concept can't be far from reality", Apr. 20, 2009, 2 pages.
Sarah Yang, "New fiber nanogenerators could lead to electric clothing", UC Regents, Feb. 12, 2010, 2 pages.
Paul Boutin, "Electric clothing? Nanofibers turn motion into electricity", VentureBeat, Feb. 12, 2010, 2 pages.

* cited by examiner

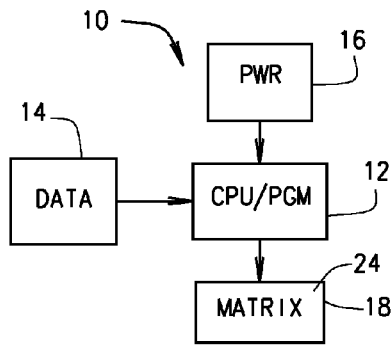
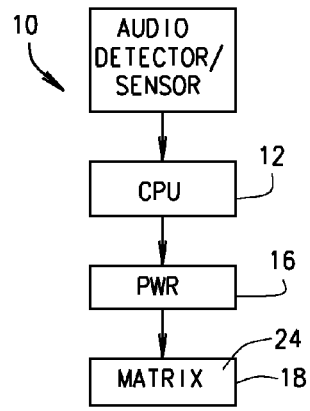
FIG. 1
FIG. 2
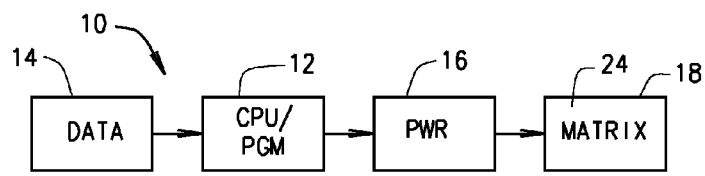
FIG. 3
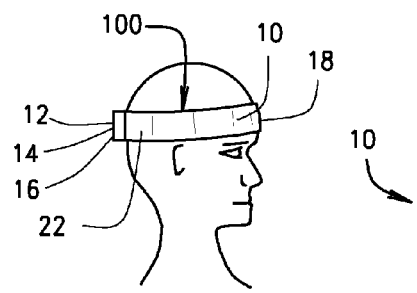
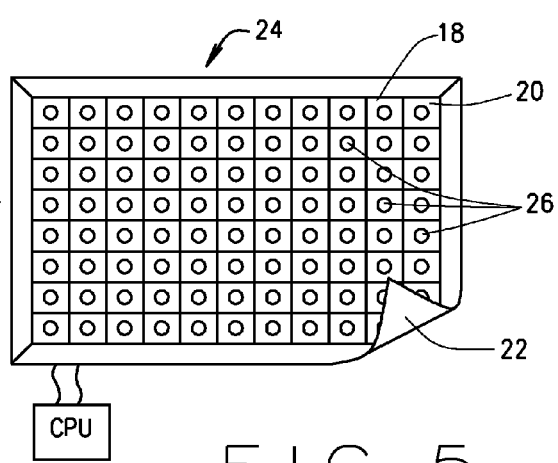
FIG. 4
FIG. 5

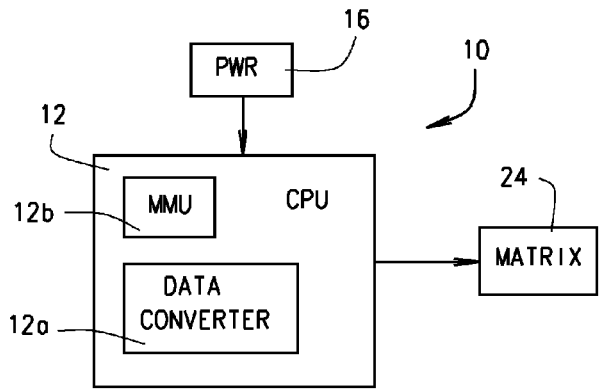
F I G . 1 1
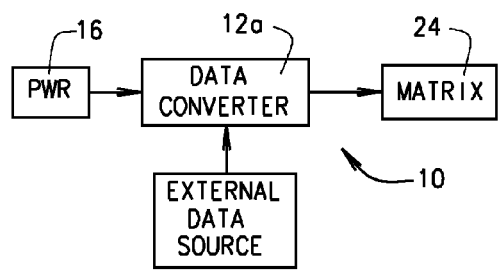
F I G . 1 2
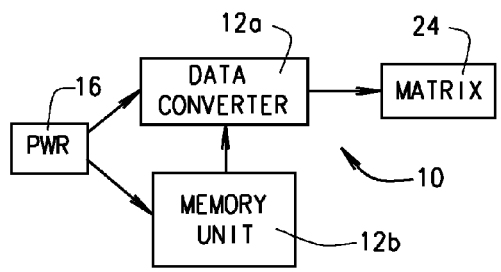
F I G . 1 3
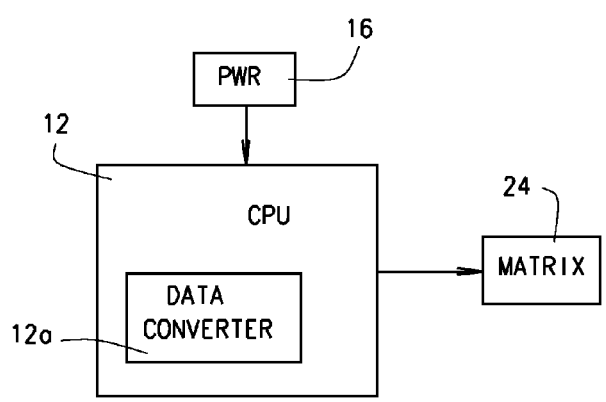
F I G . 1 4

TACTILE PATTERN MUSIC GENERATOR AND PLAYER

CROSS-REFERENCE TO RELATED APPLICATIONS

This application derives and claims priority from U.S. provisional application 61/579,416 filed 22 Dec. 2011, which application is incorporated herein by reference.

STATEMENT REGARDING FEDERALLY SPONSORED RESEARCH

Not Applicable.

BACKGROUND OF THE INVENTION

This invention relates principally to a novel device that produces tactile sensations or events discernible to human touch, and more particularly produces patterned tactile sensations or events in a fabric, or other pliable material, that are discernible by a user donning the fabric, and even more particularly to a novel device that converts electronically stored music into patterned tactile sensations or events in a matrix across a fabric. The discernible tactile sensations or events may, for example, be alternately created by retractable protrusions, contractible matrix cells, electric or temperature stimuli, and/or combinations of these.

For many years, there have existed for the purposes of entertainment countless devices that allow an individual or a multitude of individuals to listen to audio renditions of music stored in a variety of electronic formats. By way of example, such devices include speakers of all kinds in association with radios, record players, cassette players, CD players, and MP3 players. However, such devices provide limited tactile sensations for the listener, and then only indirectly or by way of a side-effect. From time to time, there have been forays into the presentation, at least in part, of creating a tactile sensation from music through vibration. However, aside from devices that directly or indirectly create musical vibrations or various braille generators, there currently exist no devices that are designed to convert electronically stored music or other audio or electronic files into tactile outputs that can be sensed or felt for entertainment.

It is therefore desirable to create a device that is capable of converting electronic files, including but not limited to music files, into patterned tactile outputs that can be sensed or felt through tactile sensations or events. Such a device may include for example, tactile outputs across a fabric that can be donned by an individual such that the individual is able to sense or feel the tactile events when the fabric is in contact with that individual's body.

BRIEF SUMMARY OF THE INVENTION

Briefly stated, the present invention sets forth a tactile pattern player comprising a matrix of tactile actuators, with each actuator configured to produce a tactile event in response to an electric impulse applied to the actuator. An electronic data storage unit and a data converter operatively associate with the actuators in the matrix. The data converter is configured to convert electronic data into electrical impulses selectively directed to the actuators in a timed sequential pattern defined by the data converter. With the tactile pattern player disposed or incorporated into the clothing of a user, the actuation of the actuators in response to the electrical impulses produces tactile sensations or events that are perceived by the user when the clothing is donned by the user.

In one embodiment, the electronic data is representative of audio data, and the data converter is configured to control the actuators to produce a tactile representation of the audio data that is perceptible to a user via contact with the user's body.

The foregoing features, and advantages set forth in the present disclosure as well as presently preferred embodiments will become more apparent from the reading of the following description in connection with the accompanying drawings.

BRIEF DESCRIPTION OF THE SEVERAL VIEWS OF THE DRAWINGS

In the accompanying drawings which form part of the specification:

FIG. 1 is a block diagram schematic of one embodiment of the novel tactile pattern player.

FIG. 2 is a block diagram schematic of another embodiment of the novel tactile pattern player.

FIG. 3 is a block diagram schematic of yet another embodiment of the novel tactile pattern player.

FIG. 4 is a perspective view of an embodiment of the novel tactile pattern player configured with the actuation matrix in a fabric headband worn about the head of a user.

FIG. 5 is a perspective view of a flexible course matrix of an embodiment of the novel tactile pattern player connected to a computer or microprocessor that controls the patterned actuation of the matrix.

FIG. 11 is a block diagram schematic of another embodiment of the novel tactile pattern player.

FIG. 12 is a block diagram schematic of another embodiment of the novel tactile pattern player.

FIG. 13 is a block diagram schematic of another embodiment of the novel tactile pattern player.

FIG. 14 is a block diagram schematic of another embodiment of the novel tactile pattern player.

Corresponding reference numerals indicate corresponding parts throughout the several figures of the drawings. It is to be understood that the drawings are for illustrating the concepts set forth in the present disclosure and are not to scale.

Figure 6:
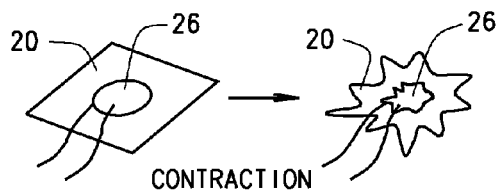
FIG. 6 is a perspective view of a contraction-type tactile actuation cell or unit of a matrix of an embodiment of the novel tactile pattern player in a relaxed state and in an actuated state following application of an electric current to the actuator.

Before any embodiments of the invention are explained in detail, it is to be understood that the invention is not limited in its application to the details of construction and the arrangement of components set forth in the following description or illustrated in the drawings.

DETAILED DESCRIPTION

The following detailed description illustrates the invention by way of example and not by way of limitation. The description enables one skilled in the art to make and use the present disclosure, and describes several embodiments, adaptations, variations, alternatives, and uses of the present disclosure, including what is presently believed to be the best mode of carrying out the present disclosure.

Figure 10:
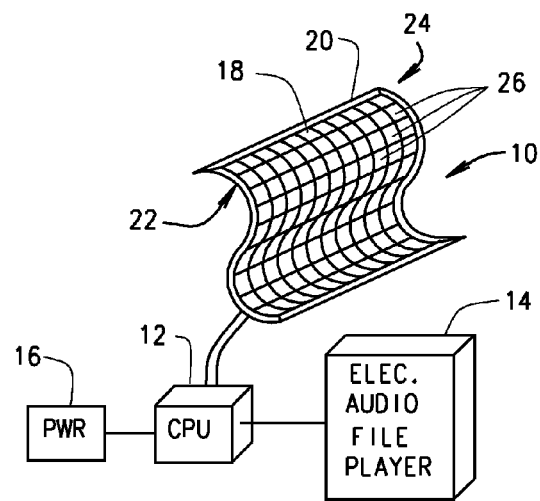
FIG. 10 is a perspective view of a flexible course matrix of an embodiment of the novel tactile pattern player connected to a computer or microprocessor that controls the patterned actuation of the matrix, and where the computer or microprocessor is operatively connected to an external electronic audio file storage device such as, for example, an MP3 player.

Referring to the drawings in general, several embodiments of the novel tactile pattern player 10 of the present disclosure are shown by way of example. As can be seen, the player 10 comprises a computer or microprocessor 12 having an integrated data converter 12a and, optionally, an integrated memory unit 12b, that is operatively connected to an electronic data storage unit 14, a battery or other power source 16, and a pliant and elastic tactile fabric 18 having an inner surface 20 and an outer surface 22. The fabric 18 comprises a matrix 24 of small and light-weight electronic tactile actuators 26 carried by the fabric 18 and operatively connected to the computer 12 and either directly or indirectly to the power source 16. (FIGS. 5, 10), where each of the actuators 26 is configured to produce a tactile event in response to an electric impulse applied to the actuator at the direction of the computer 12. Each actuator 26 is controlled by the computer 12 to selectively actuate in response to one or more signals supplied from the computer 12. Of course, the quantity, size and densities of actuators 26 comprising each matrix 24 may vary substantially from fabrics 18 having very course matrices, as depicted by way of example in FIGS. 5 and 10, to fabrics 18 having very small actuators 26 in a very dense matrix 24. Further, the matrix 24 is not limited to rectangular or square cells, but may be comprised of any variety of shaped cells and cellular alignments, such as for example, a matrix having hexagonal, octagonal or even haphazardly-shaped cells.

The computer 12 and electronic data storage unit 14 may each be further configured with one or more external connectors for receiving data from external sources. In addition, the player 10 may be configured to receive audio input (FIG. 10), from for example a tape player, a record player, an instrument pickup, or a microphone, that can be immediately converted to tactile events in the matrix 24 or that can be stored in the memory unit 12b of the player 10 for recordation and future use of the input.

In at least one embodiment, such as for example as shown in FIG. 4, the player 10 is configured to be fully portable with an associated portable power source 16, such as for example a portable battery, set of batteries or solar cell. However, in other configurations the player 10 may be configured to attach to or plug into an external power source 16 such as a power outlet, a power jack in an electronic component or other such external power source.

Figure 7:
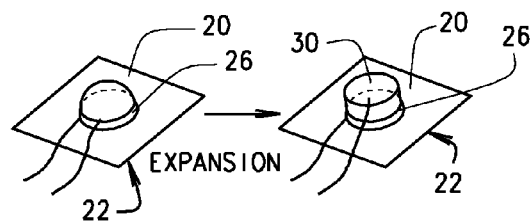
FIG. 7 is a perspective view of a protrusion-type tactile actuation cell or unit of a matrix of an embodiment of the novel tactile pattern player in a relaxed state and in an actuated state following application of an electric current to the actuator.

It can be seen in various embodiments of FIGS. 1, 10-14, that each of the actuators 26 is electrically connected through the computer 12 or the data converter 12a to the power source 16. In one embodiment, the actuators 26 are each configured to produce or generate a retractable bump or protrusion 30 (FIG. 7) in a direction opposite the outer surface 22 of the fabric 18 when stimulated by an electric impulse from the battery 16 as controlled by the computer 12. In this embodiment, the actuator 26 maintains the protrusion 30 so long as the computer applies the electric impulse to the actuator 26. The protrusion 30 retracts or relaxes when the electrical impulse ceases. Preferably, the protrusions 30, and by correlation the absence of the protrusions 30, are sized and shaped such that the actuation and emergence of the protrusion 30 is discernible by human epidermis. Likewise, the retraction and absence of the protrusion 30, such as when the protrusion 30 relaxes or retracts, is also discernible by human epidermis.

In this embodiment, the computer 12 comprises an integrated programmable data converter 12a and an integrated memory unit 12b (see FIGS. 1-3, 11-13), the data converter 12a being operatively associated with each of the actuators 26 in the matrix 24. Alternatively, the data converter 12a can be a separate component operatively associated with the computer 12 and the actuators 26. Similarly, the memory unit 12b can be a separate component operatively associated with the computer 12. The integrated data converter 12a is configured to convert electronic data stored in the memory unit 12b into electrical impulses that are then selectively directed to the actuators 26 in the matrix 24 over a period of time and in a pattern defined by the data converter 12a. The electrical impulses, as dictated by the data converter 12a, control the amplitude and the duration of each actuation of each of the actuators 26. As can be appreciated, the controlled actuation of the actuators 26 can be patterned to represent specific musical notes, tones and/or volume levels, as well as for vocals. Hence, the player 10 can, for example, replicate a musical song that has been stored in the memory unit 12b as an electronic data file by using a preprogrammed data conversion pattern stored in the data converter 12b, where the conversion pattern defines which actuators 26 in the matrix 24 to actuate, including the timing and duration of each such actuation so as to provide a patterned tactile sensation across the matrix 24 that mimics or corresponds to each of the notes and vocals in the song being played as a tactile pattern by the player 10.

The electric current or impulses that actuate the actuators 26 may be applied to the matrix 24 in a variety of manners as may be desired. For example, the electric current or impulses may be applied in a serial fashion, in a raster-scan fashion, or via independent isolated cell actuation. The ability to utilize a specific actuation manner will be dictated in part by the configuration of the interconnections between the actuators 26 and the computer 12 or the data converter 12a. That is, in order to enable the computer 12 or the data converter 12a to actuate specific actuators 26 in a matrix 24 independent of the order of actuating other actuators 26 in the same matrix 24, each actuator 26 requires its own independent set of wires or other electric current carrying mechanism connected to the computer 12 or the data converter 12a so as to allow the actuation of that particular actuator 26 without impacting the actuation of any of the other actuators 26 in the matrix 24. In contrast, for a raster-scan actuation, the actuators 26 may be connected to the computer 12 or the data converter 12a in groups—typically in rows and columns of the matrix 24—such that a rapid timed actuation of the actuators 26 can be achieved sequentially across each row or column of the matrix 24, which does not require individualized or isolated electrical connection between the computer 12 or the data converter 12a and each actuator 26.

The actuators 26 may be connected to the computer 12 or the data converter 12a by wires, conductive fibers, conductive polymers, or any other electric current carrying mechanism or device that provides the flexibility and durability as may be desired or required for construction of the various configurations of the player 10.

Preferably, the data converter 12a comprises an integrated circuit device executing a set of software instructions or a program to convert electronic data retrieved from the storage unit 12b into electrical impulses selectively directed to the actuators 26 over a period of time in a pattern defined by the program. In yet another embodiment, the data converter 12b can be user-programmable or modifiable such that a user can selectively input variable correlations between the electronic data supplied to the data converter 12b and the electric impulses directed to the actuators 26 so as to create or otherwise manipulate the conversion pattern or patterns stored in the data converter 12b that convert the electronic data to patterned actuations of the actuators 26 across the matrix 24.

Optionally, the data converter 12a may be configured with an audio-signal input port, enabling the player 10 to be operatively connected to an external source of audio signals, such as for example a personal music or data storage device, a CD player, an MP3 player, a cell phone, a cassette or other tape player, or a radio. (See, e.g., FIGS. 10, 12). Signals received via the input port may be converted by the data converter 12a into electrical impulses directed to the actuators 26, enabling the user to sense in a tactile fashion (i.e., "feel") the signals. For example, the data converter 12a may be configured to send one or more electric impulses associated with a particular musical note or vocal to an actuator or group of actuators 26 oriented in the matrix 24 such that the actuation of that actuator or group of actuators 26 corresponds to and replicates in a desired tactile sense the pitch, timbre, tone, duration, intensity, amplitude and/or resonance of the musical note or vocal.

Figure 8:
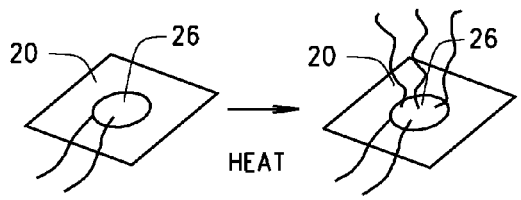
FIG. 8 is a perspective view of a heat emitting type tactile actuation cell or unit of a matrix of an embodiment of the novel tactile pattern player in a non-actuated state and in an actuated state following application of an electric current to the actuator.
Figure 9:
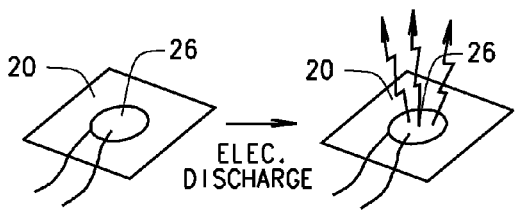
FIG. 9 is a perspective view of an electric discharge type tactile actuation cell or unit of a matrix of an embodiment of the novel tactile pattern player in a non-actuated state and in an actuated state following application of an electric current to the actuator.

The tactile events produced by the actuators 26 in response to the electrical impulses from the data converter 12a or computer 12 may comprise, for example, any one or more of the following: a retractable protrusion (FIG. 7); a retractable contraction (FIG. 6); an electric discharge (FIG. 8); a twisting or turning protrusion (not shown); a suction or pinching (not shown); or a discharge of heat (FIG. 9), depending upon the specific type of tactile actuator 26 utilized in the matrix 24. For example, the tactile actuators 26 may consist of individual micro-sized units of electro-active polymers (i.e., dielectric electro-active polymers or ionic polymers), which are essentially layered capacitors that change their capacitance when subjected to an electric current by allowing the polymer to compress in thickness and expand in area due to the electrical field. See for example, U.S. Patent Application Publication Nos. 2010/0205803 A1, 2010/0197184 A1, 2009/0293663 A1, 2010/0109486 A1, and 2008/0284277 A1, each of which are herein incorporated by reference. Alternately, by way of example, each tactile actuator 26 may define a cell consisting of a positive electric pole; a negative electric pole; and a coiled or circular dielectric positioned between and operatively associated with the positive and negative poles.

In order to facilitate improved use of the player 10 as a user-wearable article of clothing, it is preferable that the matrix 24 is pliable, and even more preferable stretchable or elastic, and housed in a fabric 18 with a means to snugly hold the matrix 24 operatively against the body of a user. (See FIGS. 4-5). In one embodiment, the player 10 is configured in the general shape of a headband 100 (FIG. 4) that can be worn about the head. In other embodiments, the player 10 can form or be incorporated into any of a variety of articles of clothing that can be worn about a portion of the user's body, such as for example, an arm, leg, or torso. Such articles of clothing can comprise for example a jacket, a hat, a glove, a scarf, a wristband, an armband, pants, shorts, socks, a leg bands, or a shirt. Referring to the headband 100 of FIG. 4 by way of example, the matrix 24 of the headband 100 may be of sufficient elasticity so as to stretch to hold the headband 100 snugly to a person's head as shown. Alternately, the fabric 18 of the headband 100 may be of sufficient elasticity so as to stretch to hold the headband 100 snugly to a person's head with the matrix 24 pressed against the user's skin. Yet, alternatively again, the headband 100 may comprise an adjustment mechanism, such as for example, a set of cords to tie the headband 100 snugly to a person's head; a set of snaps, or hooks and loops, or buttons and button holes, or other such well-known attachment devices to allow the user to snugly secure the headband 100 to the user's head. In this way, a substantial portion, if not all, of the matrix 24 is in pressed against the user's skin to provide the optimum tactile sensation for the user when the actuators 26 are activated by the player 10.

The present disclosure can be embodied in-part in the form of computer-implemented processes and apparatuses for practicing those processes. The present disclosure can also be embodied in-part in the form of computer program code containing instructions embodied in tangible media, or another computer readable storage medium, wherein, when the computer program code is loaded into, and executed by, an electronic device such as a computer, micro-processor or logic circuit, the device becomes an apparatus for practicing the present disclosure.

The present disclosure can also be embodied in-part in the form of computer program code, for example, whether stored in a storage medium, loaded into and/or executed by a computer, or transmitted over some transmission medium, wherein, when the computer program code is loaded into and executed by a computer, the computer becomes an apparatus for practicing the present disclosure. When implemented in a general-purpose microprocessor, the computer program code segments configure the microprocessor to create specific logic circuits.

As various changes could be made in the above constructions without departing from the scope of the disclosure, it is intended that all matter contained in the above description or shown in the accompanying drawings shall be interpreted as illustrative and not in a limiting sense.

What is claimed is:

1. A tactile pattern player comprising:
   a. an electric power source configured to produce one or more electric impulses;
   b. a memory unit configured to store electronic data, the electronic data comprising music;
   c. a computer processor operatively associated with the electric power source to control the production of the electric impulses, the computer processor operatively associated with the memory unit to retrieve electronic data stored in the memory unit; and
   d. a plurality of tactile actuators operatively associated with the electric power source and the computer processor, the plurality of actuators comprising a matrix, each of said actuators configured to produce a tactile event in response to one or more of said electric impulses being applied to the actuator, each such tactile event discernible by human touch;
   wherein the computer processor is programmed with a set of computer executable instructions that convert at least a portion of the electronic data stored in the memory unit into a series of commands to the power source to selectively apply a corresponding plurality of electric impulses to the plurality of actuators to produce a pattern of tactile events defined by the computer executable instructions.

2. The tactile pattern player of claim 1, wherein the electric impulses converted from the music have relative amplitudes defined by the data converter to correspond to a desired volume of the music, and at least one of the actuators generating the tactile events corresponding to the music is adapted to produce tactile events of varying amplitudes, such that the tactile events resulting from said electric impulses have amplitudes that are proportional to the amplitude of the music.

3. The tactile pattern player of claim 1, wherein the music comprises a musical note having a duration, the electric impulse converted from the musical note has a duration that is proportional to the duration of the musical note, at least one of the actuators generating the tactile events corresponding to the musical note is adapted to produce tactile events of varying durations, and the data converter controls the duration of the electric impulse.

4. The tactile pattern player of claim 1, wherein the music comprises a musical note having a pitch, a timbre, a tone, intensity, amplitude, and resonance, and the data converter generates and sends an electric impulse associated with the musical note to an actuator having a position in the matrix that corresponds to one or more of the following:
   the pitch of the musical note;
   the timbre of the musical note;
   the tone of the musical note;
   the intensity of the musical note;
   the amplitude of the musical note; and
   the resonance of the musical note.

5. The tactile pattern player of claim 1, wherein the music comprises lyrics and the pattern comprises a lyric component that generates a tactile translation of the lyrics in the music.

6. The tactile pattern player of claim 5, wherein the lyric component comprises a Braille array.

7. The tactile pattern player of claim 1, wherein the pattern is applied to the plurality of actuators in a raster scan format.

8. The tactile pattern player of claim 1, wherein the matrix is configured to be worn on a portion of a human body in such a manner that the plurality of actuators are oriented to direct their tactile events against said portion of a human body.

9. The tactile pattern player of claim 8, further comprising a clasping device configured to releasably secure the pattern player to said portion of a human body.

10. The tactile pattern player of claim 1, wherein the matrix comprises a material that is pliant.

11. The tactile pattern player of claim 1, wherein the matrix comprises a fabric.

12. The tactile pattern player of claim 1, wherein the matrix comprises a material that is elastic and is configured to stretch sufficiently to fit snugly against said portion of a human body.

13. The tactile pattern player of claim 1, wherein the computer executable instructions define the pattern using one or more of the following correlations:
   a. relative timing of sending each electric impulse to its corresponding actuator;
   b. quantity of electric impulses produced for the matrix;
   c. location within the matrix of the actuator to which one or more of the electric impulses are applied;
   d. amplitude of one or more of the electric impulses produced for the pattern; and
   e. duration of one or more of the electric impulses produced for the pattern.

14. The tactile pattern player of claim 13, wherein each of the correlations define one or more of the following:
   a. the location of each actuator to which an electric impulse is applied;
   b. the number of electric impulses applied to each actuator;
   c. the duration of one or more of the electric impulses; and
   d. the amplitude of one or more of the electric impulses.

15. The tactile pattern player of claim 13, wherein one or more of the correlations are variable.

16. The tactile pattern player of claim 13, wherein one or more of the correlations are user definable.

17. The tactile pattern player of claim 1, further comprising a user input device operatively associated with the computer processor, the computer executable instructions allowing a user to selectively input into the pattern player through the input device one or more user definable correlations between the electronic data and the electric impulses as applied to the actuators by the computer processor.

18. The tactile pattern player of claim 1, further comprising a user input device operatively associated with the computer processor, the computer executable instructions allowing a user to selectively input into the pattern player through the input device at least a portion of the electronic data converted by the computer processor into the electrical impulses applied to the actuators to produce the tactile events.

19. The tactile pattern generator of claim 1, wherein at least one of the tactile events comprises the following:
   a retractable protrusion;
   a retractable contraction;
   a twisting protrusion;
   an electric discharge; or
   a discharge of heat.

20. A tactile pattern player comprising:
   a. an electric power source configured to produce one or more electric impulses;
   b. a memory unit configured to store electronic data, at least a portion said electronic data being in a digital format;
   c. a computer processor operatively associated with the electric power source to control the production of the electric impulses, the computer processor operatively associated with the memory unit to retrieve electronic data stored in the memory unit; and
   d. a plurality of tactile actuators operatively associated with the electric power source and the computer processor, the plurality of actuators comprising a matrix, each of said actuators configured to produce a tactile event in response to one or more of said electric impulses being applied to the actuator, each such tactile event discernible by human touch;
   wherein the computer processor is programmed with a set of computer executable instructions that convert at least a portion of the electronic data stored in the memory unit into a series of commands to the power source to selectively apply a corresponding plurality of electric impulses to the plurality of actuators to produce a pattern of tactile events defined by the computer executable instructions.

21. A tactile pattern player comprising:
   a. an electric power source configured to produce one or more electric impulses;
   b. a memory unit configured to store electronic data, at least a portion of said electronic data being in an analog format;
   c. a computer processor operatively associated with the electric power source to control the production of the electric impulses, the computer processor operatively associated with the memory unit to retrieve electronic data stored in the memory unit; and d. a plurality of tactile actuators operatively associated with the electric power source and the computer processor, the plurality of actuators comprising a matrix, each of said actuators configured to produce a tactile event in response to one or more of said electric impulses being applied to the actuator, each such tactile event discernible by human touch;

wherein the computer processor is programmed with a set of computer executable instructions that convert at least a portion of the electronic data stored in the memory unit into a series of commands to the power source to selectively apply a corresponding plurality of electric impulses to the plurality of actuators to produce a pattern of tactile events defined by the computer executable instructions.

* * * * *